United States Patent [19]

Choksi et al.

[11] Patent Number: 4,820,274
[45] Date of Patent: Apr. 11, 1989

[54] MEDICAL TUBE AND/OR CABLE HOLDER

[75] Inventors: Pradip V. Choksi, 10935 Yolanda Ave., Northridge, Calif. 91326; Jamie M. Ten Napel, Pacific Palisades, Calif.

[73] Assignee: Pradip V. Choksi, Northridge, Calif.

[21] Appl. No.: 89,597

[22] Filed: Aug. 27, 1987

[51] Int. Cl.⁴ .............................................. A61M 5/00
[52] U.S. Cl. .................................. 604/174; 128/D26
[58] Field of Search .................... 128/321, 346, D26; 604/174–180

[56] References Cited

U.S. PATENT DOCUMENTS

| | | | |
|---|---|---|---|
| 3,374,509 | 3/1968 | Logan et al. | 128/D26 |
| 3,942,528 | 3/1976 | Loeser | 128/D26 |
| 4,029,103 | 6/1977 | McConnell | 128/D26 |
| 4,397,647 | 8/1983 | Gordon | 128/D26 |
| 4,611,592 | 9/1986 | Talboy | 128/321 |
| 4,639,980 | 2/1987 | Peterson | 128/D26 |
| 4,660,555 | 4/1987 | Payton | 128/D26 |

Primary Examiner—Dalton L. Truluck
Assistant Examiner—Denise Whelton
Attorney, Agent, or Firm—William W. Haefliger

[57] ABSTRACT

A medical tube or cable holder, comprises a holder body defining at least one curved path for reception of a medical tube or cable, an characterized in that the tube or cable when inserted in the path is frictionally retained therein against lengthwise displacement relative to the holder body. The body typically includes a receptacle forming the curved path, which receptacle is sidewardly open for sideward reception of the tube or cable into that path, and a cover movable into position on the receptacle to sidewardly close that path.

13 Claims, 2 Drawing Sheets

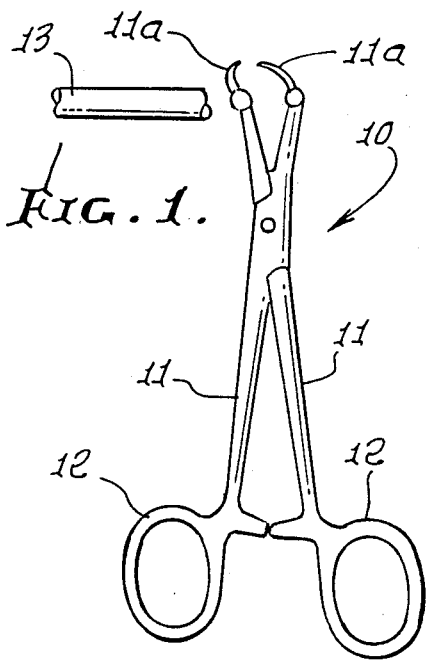
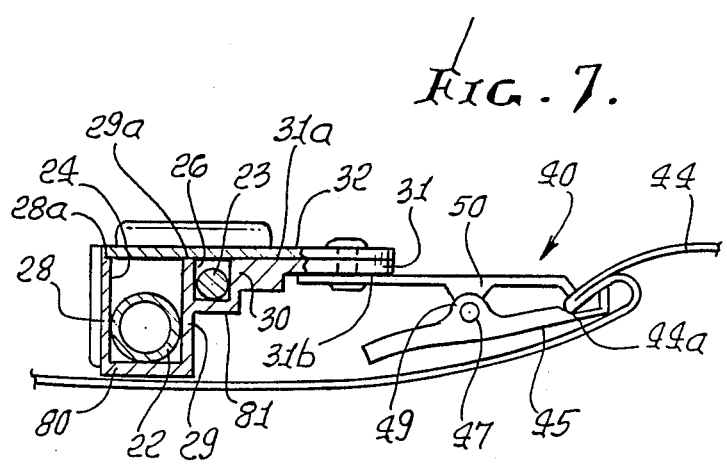
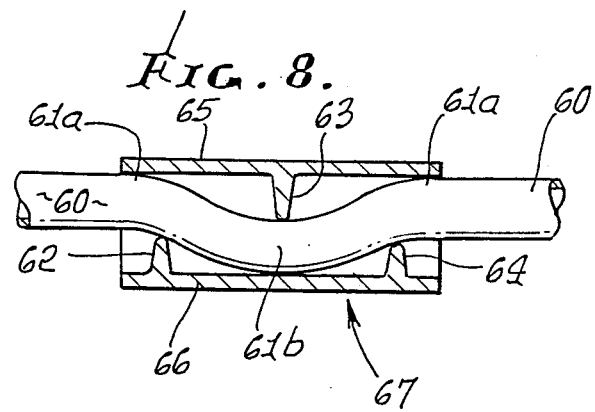
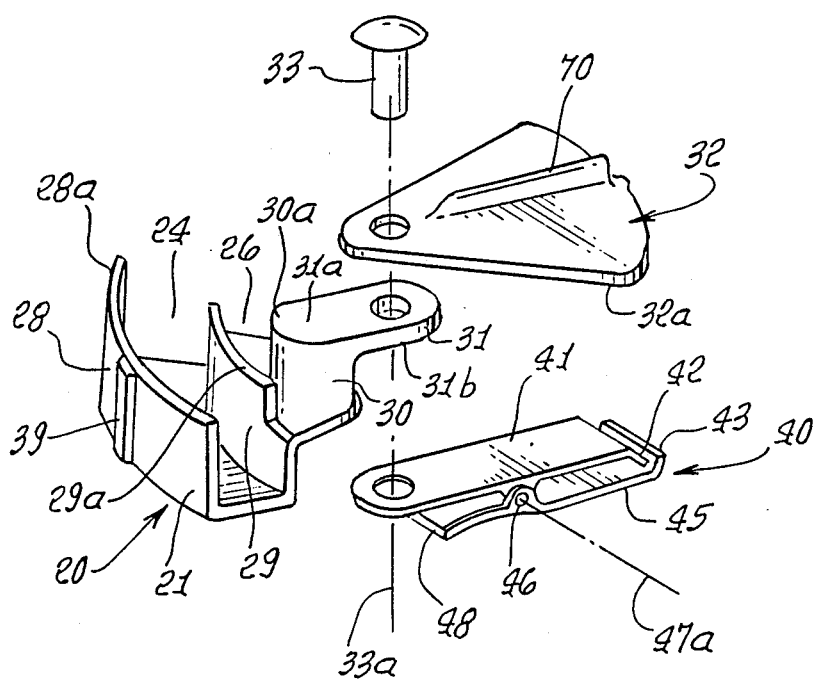

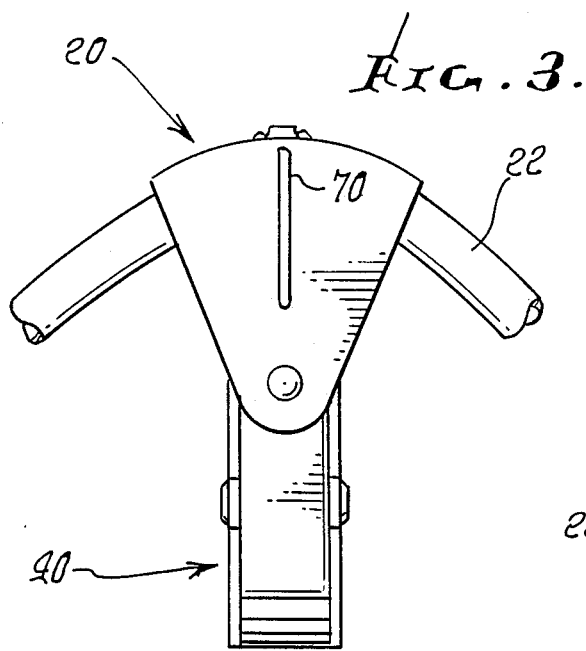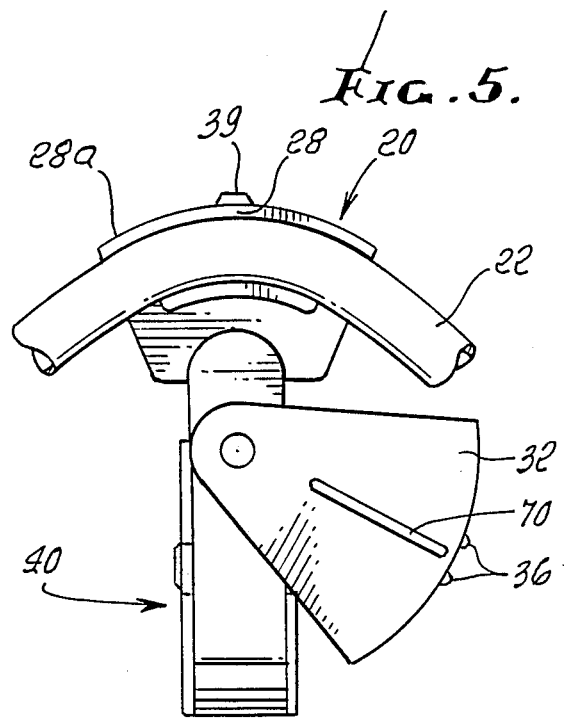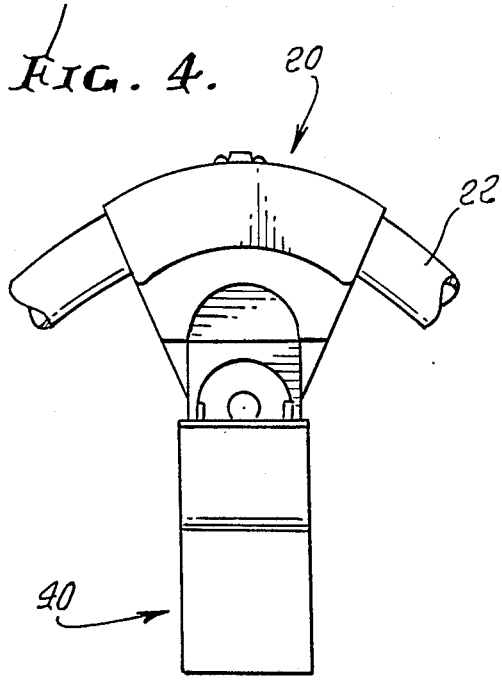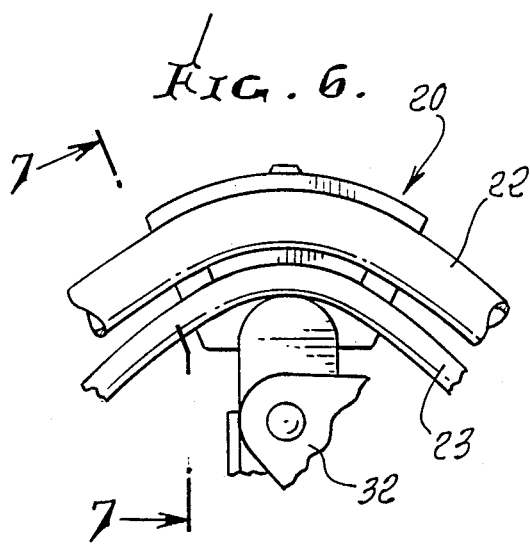

MEDICAL TUBE AND/OR CABLE HOLDER

BACKGROUND OF THE INVENTION

This invention relates generally to retention or anchoring of medical tubes and/or cables used for example during patient treatment; and more specifically the invention concerns an unusually advantageous and simple holder device for quick reception of and holding medical tube and/or cable, and which is easily anchored to fabric or other support structure for the tube or cable.

In the operating room and other areas of hospital environment tubes and cables of various sizes are used for administration of medications, suctioning and drainage of fluids from patients, monitoring of vital functions, and performing electrical cauterization. It is important that these tubes and cables be secured to either the bed sheet or surgical drape so that they do not fall to the floor and get contaminated or tangled.

At present time the commonly used means of holding a tube or cable is with a scissors-like towel clamp, which punctures the drape and holds securely. The tube or cable is threaded through the loop of the towel clamp; however, even with the towel clamp held securely to the drape, the tube can slide back and forth in the loop and can become contaminated by falling to the floor or outside the sterile field. The towel clamp puncture of the drape is not desirable because contaminants can then penetrate the sterile drape.

SUMMARY OF THE INVENTION

It is a major object of the invention to provide improved means for holding and anchoring a medical tube and/or cable, in a medical or hospital environment. Basically, the invention is embodied in a medical tube and/or cable holder which comprises:

(a) a holder body defining at least one curved path for reception of a medical tube or cable, and characterized in that the tube or cable when inserted in said path is frictionally retained therein against lengthwise displacement relative to the holder body, (b) and means attached to said body for anchoring the body and a tube or cable received in said path to support fabric associated with said tube or cable.

As will appear, the body typically includes a receptable forming said path which is sidewardly open for sideward reception of the tube or cable into said path, and a cover movable into position on the receptacle to sidewardly close said path. The cover may be pivotally attached to the receptacle to swing into and out of said path closing position; and the holder structure may include detent means on the cover and receptacle for releasably holding the cover in said path closing position.

Further, the body may typically form two of said curved paths, one of which has a cross section larger than the other; and a medical tube may be retained in said one path, and a medical cable retained in the other path. In this regard, the body may typically have walls that form two of said curved paths, said cover swingable into position over said walls for covering both of said paths, simultaneously.

In addition, the anchoring means may advantageously have pivotal attachment to the body and comprise clamp means; and both the cover and clamp means may have the same axis of pivoting, these elements swingable at opposite sides of a mounting plate defined by the holder body structure.

These and other objects and advantages of the invention, as well as the details of an illustrative embodiment, will be more fully understood from the following specification and drawings, in which:

DRAWING DESCRIPTION

FIG. 1 is a perspective view of a conventional tube holder;

FIG. 2 is an exploded perspective view of a tube and/or cable holder embodying the present invention;

FIG. 3 is a top plan view of the FIG. 2 holder;

FIG. 4 is a bottom plan view of the FIG. 2 holder;

FIG. 5 is a view like FIG. 3, with the cover swung sidewise to permit tube replacement;

FIG. 6 is a view like FIG. 5 showing electrical cable retention by the holder;

FIG. 7 is an enlarged side elevation on lines 7—7 of FIG. 6; and

FIG. 8 is a section showing an alternative holder with tubing deflected path retention.

DETAILED DESCRIPTION

In FIG. 1, a conventional scissors-like "towel" clamp 10 has arms 11 with tips 11a that puncture the drape or towel; these arms 11 form a loop 12 through which medical tubing (such as intravenous fluid flow tubing) 13 is threaded. Even with the clamp held securely to the punctured drape (or sheet or towel) the tubing 13 can slide back and forth in the loop. These are substantial disadvantages.

FIGS. 2-7 show an embodiment of the present invention which incorporates material and unusual advantages. The medical tube and/or cable holder 20 of the present invention includes a holder body 21 defining at least one curved path for reception of a medical tube or cable, and characterized in that the tube or cable when inserted in said path is frictionally retained therein against lengthwise displacement relative to the holder body. Also, the holder 20 includes means 40 attached to body 21 for anchoring it and the received tube and/or cable to support fabric associated with the tube or cable. FIGS. 6 and 7 show tubing at 22, cable at 23, and support fabric (towel, sheet or drape) at 44a.

More specifically, the body 21 may consist of hard, molded plastic material and define a receptacle forming two paths, i.e. first curved path 24 which is sidewardly open for easy, close-fitting, sideward top reception of the larger diameter tube or tubing 22; and second curved path 26 which is sidewardly open for easy, close-fitting, sideward reception of the smaller diameter electrical cable (or other tubing) 23. The two paths are generally parallel through their arcuate, generally circular extents of between 30° and 90°, for best results, including sufficient curvature to frictionally retain the tubing and cable in curved conformation against endwise slippage, concomitant with least deviation and pinching of the tubing. Also, the curved, parallel relation of the two paths, keep the tubing and cable separated from one another. Sideward entry of the tubing and cable enables easy fitting of the holder to existing deployed tubing and/or cable, anywhere along the length thereof.

Note in FIG. 7 that the paths 24 and 26 are channel shaped in cross section, along their lengths; path 24 defined by and between generally circularly curved upstanding walls or ribs 28 and 29; and path 26 defined by and between rib 29 and curved rib 30. Webs 80 and 81 connect the ribs 28 and 29, and 29 and 30, web 81 being at higher elevation than web 80. These ribs have uppermost edges 28a, 29a and 30a in a common plane defined by the top surface 31a of a horizontal body plate 31. Path 24 is larger in cross section than path 26.

The body includes a cover 32 movable into and out of position (seen in FIG. 3) on the receptacle to sidewardly close the path or paths 24 and 26, blocking sideward escape of the tubing and/or cable from either or both paths. As illustrated, the cover is advantageously pivotally attached to the receptacle, as by a pivot pin 33 defining upright pivot axis 33a, to swing into that position (see FIG. 2), and to swing out of that position (see FIG. 5) enabling insertion of the tubing and/or cable into the curved paths, or to enable their sideward removal from those paths. Note that the cover underside 32a swings in the plane defined by surface 31a and terminal edges 28a, 29a and 30a, to closely bridge those edges when the cover is swung to closed position, whereby the cover is supported by those edges, and blocks escape of the tubing and/or cable from the curved retention paths. A rib 70 on the top of cover 32 projects upwardly for finger engagement to swing the cover.

Detent means is provided on the cover and receptacle to releasably retain the cover in path closing position. See for example the tongue 36 on the cover rim 37, that projects for engagement with and on two sides of the rib 39 that projects above the terminal edge 28a, in FIGS. 3 and 5.

The clamp means 40 is shown to include a plate 41 pivotally attached, as by pin 33, to plate 31, to swing horizontally at the underside 31b of plate 31. The plate 41 terminates at a jaw 42 cooperating with a second jaw 43 to grip a portion 44a of drape or fabric 44. Second jaw 43 is on an arm 45 that is pivotally attached at 46 to plate 41, whereby arm 45 pivots about a horizontal axis 47a generally normal to and offset from axis 33a. Note handle 48 on arm 45, and upturned tangs 49 on arm 45 overlapping downturned tangs 50 on plate 41, to which a pivot pin 47 connects. Thus, the holder may swivel about axis 33a, relative to the clamp means attached to the fabric 44. A torsion spring, not shown, wrapped about pin 47, urges jaw 43 toward jaw 42.

Unique and advantageous features of the holder include:
1. It holdes one or more tube, simultaneously.
2. It holds tubes and cables without pinching them. The flow through the tubes is not impeded.
3. It accomodates significant variation in tubing diameter.
4. It prevents axial sliding of the tubing.
5. The clip does not puncture the drape, yet holds securely.
6. Pivoting action of the clip and main body of the tube holder allows easy manipulation of the tubing without excessive tugging.
7. It is compact in size, compared to standard towel clamps.
8. It is very easy to use.

FIG. 8 shows a variation in the holder body, providing a curved path for the tubing 60, that path having wave shape, with at least two crests 61a and one trough 61b. This is accomplished by projections 62–64 on the walls 65 and 66 of the holder body 67. Wall 65 is close toward wall 66 to enable sideward insertion of the tubing therefrom.

We claim:
1. A medical tube or cable holder, comprising:
   (a) a holder body defining at least one curved path for reception of a medical tube or cable, and characterized in that the tube or cable when inserted in said path is frictionally retained therein against lengthwise displacement relative to the holder body,
   (b) and means attached to said body for anchoring the body and a tube or cable to be received in said path to support fabric associated with said tube or cable,
   (c) said body including a receptacle forming said path which is sidewardly open for sideward reception of the tube or cable into said path, and a cover movable into position on the receptacle to sidewardly close said path, the cover being pivotally attached to the receptacle to swing into and out of said path closing position,
   (d) the body also defining a plate projecting away from said path, the cover and the anchoring means both pivotally attached to that plate.

2. The holder of claim 1 including detent means on the cover and receptacle for releasably holding the cover in said path closing position.

3. The holder of claim 1 wherein said body forms two said curved paths, one of which has a cross section larger than the other.

4. The holder of claim 3 including a medical tube retained in said one path, and a medical cable retained in the other path.

5. The holder of claim 1 wherein said body has walls that form said one curved path and also a second curved path, said cover swingable into position over said walls for covering both of said paths, simultaneously.

6. The holder of claim 5 wherein one of said paths has a cross section larger than the other, said walls having terminal edges in the same plane sidewardly of said paths to be closely bridged by said cover when the cover is swung into path closing position.

7. The holder of claim 6 including interengagable detent means on the cover and receptacle to releasably retain the cover in path closing position.

8. The holder of claim 1 wherein the said means for anchoring has pivotal attachment to said body and comprises clamp means.

9. The holder of claim 1 wherein the cover and anchoring means extend at opposite sides of the plate and have a common pivoting axis.

10. The holder of claim 9 wherein the receptacle and cover consist of molded plastic material.

11. The holder of claim 1 wherein said path extends generally circularly throughout an arc between 30° and 90°.

12. The holder of claim 1 wherein said path extends generally as a wave having at least two crests and one trough.

13. A medical tube or cable holder, comprising:
   (a) a holder body defining at least one curved path for reception of a medical tube or cable, and characterized in that the tube or cable when inserted in said path is frictionally retained therein against lengthwise displacement relative to the holder body,
   (b) and means attached to said body for anchoring the body and a tube or cable to be received in said path to support fabric associated with said tube or cable,
   (c) said body including a receptacle forming said path which is sidewardly open for sideward reception of the tube or cable into sid path, and a cover movable into position on the receptacle to sidewardly close said path, the cover being pivotally attached to the receptacle to swing into and out of said path closing position, (d) the body having walls that form said one curved path and also a second curved path, said cover swingable into position over said walls for covering both of said paths, simultaneously, one of said paths having a cross section larger than the other, said walls having terminal edges in the same plane sidewardly of said paths to be closely bridged by said cover when the cover is swung into path closing position, (e) the means for anchoring having pivotal attachment to the body and comprising clamp means, the pivotal attachment of both the clamp means and cover having the same axis of pivoting.

* * * * *